United States Patent [19]
Marin et al.

[11] Patent Number: 5,397,355
[45] Date of Patent: Mar. 14, 1995

[54] INTRALUMINAL STENT

[75] Inventors: Michael L. Marin; Ralph Marin, both of New York, N.Y.

[73] Assignee: Stentco, Inc., Elmwood Park, N.J.

[21] Appl. No.: 278,546

[22] Filed: Jul. 19, 1994

[51] Int. Cl.$^6$ .............................. A61F 2/04
[52] U.S. Cl. ............................... 623/12
[58] Field of Search ............... 623/1, 11, 12; 606/191–200, 151–158; 411/74, 71, 61; 138/108, 112

[56] References Cited

U.S. PATENT DOCUMENTS

| | | | |
|---|---|---|---|
| 3,910,156 | 10/1975 | Soltysik | 411/61 |
| 4,657,456 | 4/1987 | Anguetin | 411/61 |
| 5,018,919 | 5/1991 | Stephan | 411/61 |
| 5,330,500 | 7/1994 | Song | 606/198 |

*Primary Examiner*—David Isabella
*Assistant Examiner*—Debra S. Brittingham
*Attorney, Agent, or Firm*—Darby & Darby

[57] ABSTRACT

An improved stent provides mechanical anchoring of the stent to a blood or other body vessel. The stent has, in a preferred embodiment, barbs which remain within the surface of the stent when the stent is in its unexpanded condition, but which extend from the surface of the stent when the stent is expanded. These barbs are adapted to engage, for example, a graft and/or the inner layers of a blood vessel to mechanically attach the stent to the vessel. Because friction is not solely relied upon to hold the stent in place, the stent may exert less force on the blood vessel which, in turn, means that a thinner stent requiring less force for expansion may be used. In addition, there may be less radial force permanently exerted in an artery after stent deployment which may be less injurious to the vessel.

6 Claims, 1 Drawing Sheet

INTRALUMINAL STENT

FIELD OF THE INVENTION

This invention relates to intraluminal stents and, more particularly, to intraluminal stents of the type used to retain a grafted stent within a blood vessel.

BACKGROUND OF THE INVENTION

Endoluminal grafts have been used to repair blood vessels affected with any of a variety of lesions which can compromise circulation through the blood vessel to a portion of the body. The graft may be made of dacron, expanded polytetrafluoroethelyne (ePTFE), or a natural substitute such as a vein or artery taken from another portion of the body. Typically, the graft is held in place within a blood vessel by means of an expandable stent.

A variety of different stents have been used and proposed for this purpose. One stent, known as a Palmaz stent, has been used as a means for anchoring a graft within a blood vessel. The Palmaz stent is illustrated in FIGS. 1A and 1B of Palmaz U.S. Pat. No. 5,102,417. In this patent, the Palmaz stent is characterized as an "expandable intraluminal graft" The patent contains an extensive description of the prior art and the problems which the Palmaz stent was designed to overcome. U.S. Pat. No. 5,102,417 (the "Palmaz patent") and its parents are hereby incorporated by reference into this specification.

The basic Palmaz stent comprises a mesh-like tubular member which can be expanded from a first diameter to a second diameter. The stent may be expanded by means of a balloon catheter, the force applied by the balloon exceeding the elastic limit of the stent so that when the balloon is deflated, the stent remains in its expanded form. Since expansion of the stent can be closely controlled, if the stent is expanded into contact with the surface of a blood vessel, a graft positioned between the stent and blood vessel can be secured within the blood vessel.

As explained in the Palmaz patent, the Palmaz stent provides benefits in addition to the ability to anchor a graft at a desired location within a blood vessel. For example, the stent can be used by itself to prevent the recurrence of stenoses, and to prevent recoil of an elastic vascular stenosis. It is usable in critical vessels such as the left main coronary artery where the possibility of the intimal flap blocking blood flow limits the use of balloon dilatation procedures.

SUMMARY OF THE INVENTION

The present invention provides an improvement over the basic Palmaz stent in that it provides a means for mechanically anchoring the stent to the blood vessel. In the preferred embodiment, these means comprise barbs which remain within the surface of the stent when the stent is in its unexpanded condition, but which extend from the surface of the stent when the stent is expanded. These barbs are adapted to engage the graft and the surface of the blood vessel to mechanically attach the stent to the vessel. Because friction is not solely relied upon to hold the stent in place, the stent may exert less force on the blood vessel which, in turn, means that a thinner stent requiring less force for expansion may be used. In addition, there may be less radial force permanently exerted in an artery after stent deployment which may be less injurious to the vessel.

DETAILED DESCRIPTION OF THE INVENTION

In its preferred embodiment, the invention is intended to be used as part of a stented graft, but it is contemplated that the invention would have utility for other purposes, including but not limited to the purposes itemized in the Palmaz patent.

Delivery and deployment of a stent in accordance with the invention may be by conventional means including, but not limited to, the balloon catheters disclosed in the Palmaz patents. The mechanical delivery and deployment means disclosed in U.S. patent application Ser. No. 08/196,278 filed on Feb. 10, 1994, in the names of Michael and Ralph Marin and entitled APPARATUS AND METHOD FOR DEPLOYMENT OF RADIALLY EXPANDABLE STENTS BY A MECHANICAL LINKAGE may also be used. Since the device for delivering and deploying the stent forms no part of this invention, it is neither illustrated nor described in this application.

Figure 1:
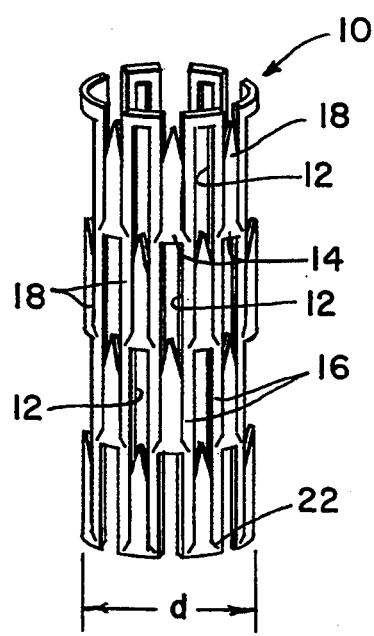
FIG. 1 is a perspective view of a preferred embodiment of the invention showing the stent in its unexpanded condition.

Referring now to the drawings, a stent comprises a tubular mesh-like member 10. The stent may be made from a stainless steel tube or other metal in which elongated openings 12 are cut, for example by conventional laser cutting techniques or electrical discharge machining. Removal of the tubular material to form the elongated openings 12 results in a multiplicity of intersecting members which may be characterized as circumferential ribs 14 and bars 16 which are colinear with the axis of the tube. As shown in FIG. 1, each of the circumferential ribs 14 intersects one of the colinear bars 16 at the halfway point of an adjacent rectangular opening 12.

As explained in the Palmaz patents, the stent may be made of various materials, but a thin-walled stainless steel tube is preferred. The material must deform when pressure is applied to the interior surface of the tubular member (for example by means of a balloon) and, of course, must be strong enough to withstand any pressure applied by the blood vessel (or other body lumen) in which it is to be placed.

Figure 2:
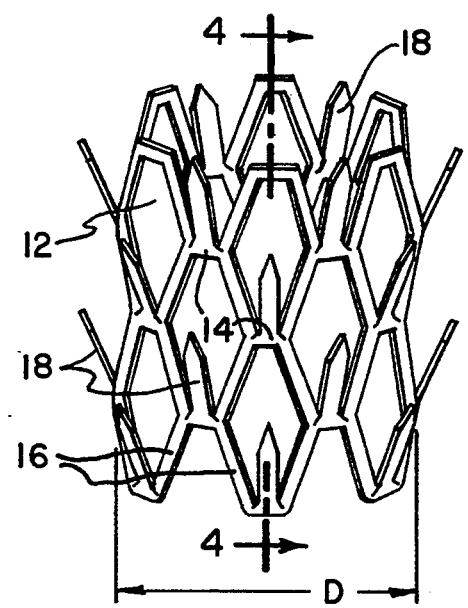
FIG. 2 is a perspective view of the stent of FIG. 1 in its expanded condition.

The diameter of the unexpanded stent is shown at "d" in FIG. 1. When pressure is applied to the interior surface of the stent, the colinear bars 16 are deformed causing the openings 12 to assume a diamond-like shape. By virtue of this deformation of the bars 16, the diameter of the stent increases from "d" to "D", with the length of the stent being reduced proportionately to accommodate the increase in diameter (compare FIG. 1 with FIG. 2).

Figure 3:
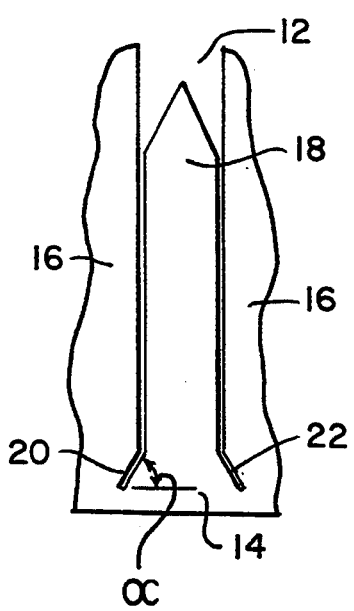
FIG. 3 is an exploded view of a portion of the stent showing the manner in which the barb is connected to the mesh-like wall of this stent.
Figure 4:
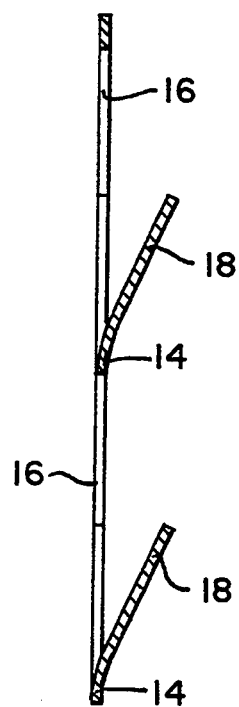
FIG. 4 is a sectional view along the line 4—4 of FIG. 2.

In accordance with the invention, a barb 18 extends into each of the elongated openings 12 from a circumferential rib 14 at one end of the opening. Each of the barbs lies flat in the surface of the tubular member in its unexpanded state. It has been discovered that if a pair of oblique slots 20 and 22 (see FIG. 3) are provided in the circumferential rib 14 at its juncture with the barb 18, when a force is applied to the inner surface of the stent, expansion of the stent will cause the barb 18 to move radially outwardly from the surface of the stent as it expands (see FIG. 4). In other words, as the stent is deployed, the barbs 18 are also deployed so that when the stent contacts the surface of the blood vessel, the barbs penetrate the inner lining of the blood vessel to anchor the stent in place.

The dimensions of the components of the stent, including the barb are not critical and may be determined empirically. It is believed that the angle α illustrated in FIG. 3 should be between 30° and 60°, optimally 45°. Likewise the length of the slots 20 and 22 may be determined empirically with a view toward optimizing the deployment of the barbs without weakening excessively the circumferential ribs 14. The slots 20 and 22 serve an important function in causing the barbs to deploy during expansion of the stent.

It is also possible that opposing barbs 18 may extend toward each other in each slot 12. In other words, two barbs 18 would extend in opposite directions from each circumferential rib 14. This, of course would double the number of barbs, which would enhance attachment of the stent to the blood vessel.

Figure 5:
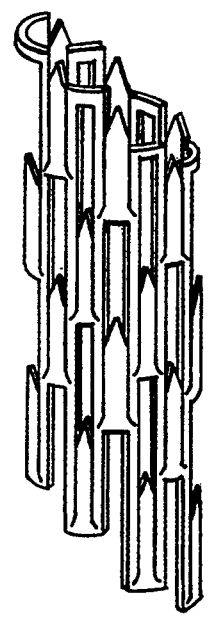
FIG. 5 is a perspective view of a modification of the preferred embodiment showing the stent in its unexpanded condition with a staggered arrangement of circumferential ribs.

Also contemplated is a stent having a staggered arrangement of circumferential ribs 14 as shown in FIG. 5. By staggering or displacing the circumferential ribs 14 as shown in FIG. 5, expansion of the stent will create forces in an oblique direction which may increase the strain in the ribs 14 and thereby magnify the force on the junction between each barb 18 and rib 14.

Many modifications of the illustrated embodiment are possible within the scope of the invention. The illustrated embodiment is therefore to be considered in all respects as illustrative and not restrictive; the scope of the invention being indicated by the appended claims, and not limited to the foregoing description.

What is claimed is:

1. An implantable intraluminal stent, comprising a tubular wall defined by a multiplicity of intersecting members forming a multiplicity of openings, said tubular wall being expandable from a first diameter to a second diameter upon application of a radially directed force to the interior surface of said wall, at least some of said intersecting members including a barb, each said barb lying flat in the surface of said tubular wall when it is unexpanded and extending out of the surface of said tubular wall for engagement of a lumen when it is expanded.

2. A stent according to claim 1, wherein said barbs are colinear with the axis of said tubular wall.

3. A stent according to claim 2, wherein said intersecting members include circumferential ribs, said barbs extending from said ribs.

4. A stent according to claim 1, wherein oblique slots are formed in said ribs at each intersection of a barb and rib.

5. A stent according to claim 2, wherein oblique slots are formed in said ribs at each intersection of a barb and rib.

6. A stent according to claim 3, wherein oblique slots are formed in said ribs at each intersection of a barb and rib.

* * * * *